United States Patent [19]
Lee et al.

[11] Patent Number: 6,059,815
[45] Date of Patent: May 9, 2000

[54] MICROFABRICATED THERAPEUTIC ACTUATORS AND RELEASE MECHANISMS THEREFOR

[75] Inventors: Abraham P. Lee, Walnut Creek; Joseph P. Fitch, Livermore; Daniel L. Schumann, Concord; Luiz Da Silva, Danville; William J. Benett, Livermore; Peter A. Krulevitch, Pleasanton, all of Calif.

[73] Assignee: The Regents of the University of California, Oakland, Calif.

[21] Appl. No.: 09/067,824

[22] Filed: Apr. 28, 1998

Related U.S. Application Data

[63] Continuation-in-part of application No. 08/807,412, Feb. 28, 1997, Pat. No. 5,911,737.

[51] Int. Cl.[7] .................................................. A61B 17/28
[52] U.S. Cl. ............................................................ 606/209
[58] Field of Search ................................... 606/209, 206, 606/207, 205–211; 604/164

[56] References Cited

U.S. PATENT DOCUMENTS 5,762,630  6/1998  Bley et al. ............................... 604/164

*Primary Examiner*—Michael Buiz
*Assistant Examiner*—Kevin Truong
*Attorney, Agent, or Firm*—L. E. Carnahan; Alan H. Thompson

[57] ABSTRACT

Microfabricated therapeutic actuators are fabricated using a shape memory polymer (SMP), a polyurethane-based material that undergoes a phase transformation at a specified temperature (Tg). At a temperature above temperature Tg material is soft and can be easily reshaped into another configuration. As the temperature is lowered below temperature Tg the new shape is fixed and locked in as long as the material stays below temperature Tg. Upon reheating the material to a temperature above Tg, the material will return to its original shape. By the use of such SMP material, SMP microtubing can be used as a retaining/release actuator for the delivery of material, such as embolic coils, for example, through catheters into aneurysms, for example. The microtubing can be manufactured in various sizes and the phase change temperature Tg is determinate for an intended temperature target and intended use. The SMP microtubing can be positioned around or within an end of a deposit material. Various heating arrangements can be utilized with the SMP release mechanism, and the SMP microtubing can include a metallic coating for enhanced light absorption.

18 Claims, 5 Drawing Sheets

MICROFABRICATED THERAPEUTIC ACTUATORS AND RELEASE MECHANISMS THEREFOR

RELATED APPLICATION

This application is a continuation-in-part of U.S. application Ser. No. 08/807,412 filed Feb. 28, 1997 now U.S. Pat. No. 5,911,737 issued Jun. 15, 1999, entitled "Microfabricated Therapeutic Actuators," and assigned to the same assignee.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microfabricated actuators, particularly to microactuators for use in catheter-based interventional therapies or remote micro-assembly applications, and more particularly to microfabricated therapeutic actuators utilizing shape memory polymer (SMP) microtubing as a release actuator mechanism, and to heating arrangements for SMP release mechanisms.

Microactuators for remote and precise manipulation of small objects is of great interest in a wide variety of applications. Recently, substantial efforts have been directed to the development of microactuators or microgrippers for various application, and which are particularly useful in the medical field, such as for catheter-based intervention therapies and remote assembly or use of micromechanical systems. There has been particular interest in the development of microactuators capable of operating in small (250–500 μm) diameter applications, such as in veins and arteries in the human brain, which enables catheter-based devices to reach and treat an aneurysm in the brain.

A recent approach to satisfying this need involves microactuators or microgrippers fabricated using known silicon-based techniques or precision micromachining, or a combination of these techniques, with the microgrippers being actuated, for example, by balloons or by shape-memory alloy (SMA) films or wires deposited on or connected to the jaws of the microgrippers. Such an approach is described and claimed in U.S. Pat. No. 5,645,564 issued Jul. 8, 1997, entitled "Microfabricated Therapeutic Actuator Mechanism," assigned to the same assignee. Another recent approach involves a miniature plastic gripper constructed of either heat-shrinkable or heat-expandable plastic tubing having a cut in one end section to form gripping surfaces or jaws which are moved by inflation or deflation of an associated microballoon. Such an approach is described and claimed in U.S. Pat. No. 5,609,608 issued Mar. 11, 1997, entitled "Miniature Plastic Gripper And Fabrication Method," assigned to the same assignee. Also, microdevices for positioning, steering, and/or sensor applications have been developed which utilize blood flow for positioning and steering of catheter-based therapeutic applications. Such microrudders, microactuators or microcantilevers are described and claimed in copending U.S. application Ser. No. 08/533,426, filed Sep. 25, 1995, entitled "Micromachined Actuators/Sensors For Intratubular Positioning/Steering," now U.S. Pat. No. 5,771,902 issued Jun. 30, 1998, assigned to the same assignee. In addition, recent efforts have been directed to the fabrication of micromolds for the production of microballoons used, for example, for angioplasty to perform interventional catheter-based minimal-invasive surgeries, wherein microballoons or microneedles having, for example, a 275 μm length and 150 μm diameter can be readily manufactured. Such a micromold is described and claimed in U.S. Pat. No. 5,658,515, issued Aug. 19, 1997, entitled "Polymer Micromold And Fabrication Process".

Patients with potentially life-threatening hemmorhagic brain aneurysms are in need of a safe, reliable, and fast release mechanism for the deposition of embolic platinum coils via catheters. The commercial product of current use is the Guglielmi Detachable Coil (GDC). The GDC utilizes the electrolytical dissolution of a designated guidewire junction to generate the release action. This procedure typically takes 10–30 minutes and is difficult to control in a reliable fashion. The effects of the dissolved material into the blood stream is also a potential hazard to the patient. Thus, even with the numerous prior efforts to develop miniature actuators for catheter-based therapeutic application, there remains a need for safe, fast release actuator mechanisms for the delivery of embolic coils, for example.

More recently, efforts have been directed to satisfy this need based on the use of a shape memory polymer (SMP), a polyurethane-based material that undergoes a phase transformation at a manufactured temperature (Tg) of choice. After the material is polymerized (cross-linked), the material is molded into its memory shape. At temperatures above Tg, the material can be easily reshaped into another configuration, and upon cooling below Tg the new shape is fixed, but upon increasing the temperature to above Tg, the material will return to its original memory shape. By inserting one end of a coil, for example, into an end of a SMP microtube, and applying pressures to the outside of the microtube while at a temperature above the Tg and then lowering the temperature below the Tg, the coil is secured and retained in the microtube. After inserting the microtube and retained coil via a catheter to a desired location, the SMP microtube is locally heated to above Tg and it returns to its original shape releasing the coil, after which the microtube is withdrawn leaving the coil in place. Therapeutic actuators utilizing shape memory polymer (SMP) microtubing are described and claimed in above-referenced U.S. application Ser. No. 08/807,412, now U.S. Pat. No. 5,911,737.

The present invention relates to therapeutic actuators utilizing SMP retention/release mechanisms and to heating options for SMP release mechanisms. In addition to embodiments involving the insertion of an end of a deposit material into the SMP tubing for retention thereby, the SMP tubing is inserted into an end of a deposit material which is retained thereby by expansion of the inserted SMP tubing (an inverted grip mechanism). The SMP heating options include resistive heating, optical laser light heating, and external field (RF, magnetic induction) heating. Also by coating the exterior of the SMP tubing with a reflective material enhanced light absorption in the SMP tubing is provided.

SUMMARY OF THE INVENTION

It is an object of the present invention to provide a microfabricated therapeutic actuator.

A further object of the invention is to provide a heating mechanism for a release actuator mechanism using shape memory polymer (SMP) materials.

A further object of the invention is to provide SMP materials with a light absorbing coating.

A further object of the invention is to utilize shape memory polymer (SMP) microtubing as a release actuator for the delivery of material to a point of use.

A further object of the invention is to provide heating means for SMP release mechanisms.

Another object of the invention is to provide a release actuator mechanism which utilizes shape memory polymer microtubing for use in catheter-based intratubular delivery of material (e.g. embolic coils) to a point of need.

Another object of the invention is to provide inverted SMP tubing configurations for a release actuator.

Another object of the invention is to provide microfabricated therapeutic actuators constructed of shape memory polymer microtubing, wherein the shape memory is determined by a desired temperature of the application for the microtubing.

Another object of the invention is to provide a release actuator utilizing a shape memory polymer and which can be designed for remote medical applications, safety latches, connectors, assembly of read-write heads for disk drives, and other remote applications wherein a reliable and relatively fast release time is desired.

Another object of the invention is to provide heating arrangements for SMP material which include laser light heating, resistive heating, and external field heating.

Other objects and advantages of the present invention will become apparent from the following description and accompanying drawings. Basically, the invention involves improvements in the microfabricated therapeutic actuators of above-referenced U.S. application Ser. No. 08/807,412. More specifically, the invention involves using shape memory polymer (SMP) microtubing as a release actuator mechanism, for example, as a means for the delivery of embolic coils through catheters into aneurysms with optional heating mechanisms for the SMP microtubing. The release actuator mechanism aside from its medical applications can be utilized for safety latches, connectors, product delivery, assembly of read-write heads for disk drives, etc. The SMP microtubing particularly provides a safe, reliable, and fast release mechanism for deposition of embolic platinum coils, for example, via catheters for patients with potentially life-threatening hemmorhagic brain aneurysms, wherein the speed of release is in seconds compared to the 10–30 minutes required for deposition of a conventionally used Guglielmi Detachable Coil (GDC). Further, the SMP microtubing release mechanism provides no potential hazard to the patient, such as that resulting from the electrolytical dissolution of the guidewire junction currently used to release the GDC. The SMP material is a polyurethane-based material that undergoes a phase transformation at a manufactured temperature (Tg). The SMP material can be constructed so as to be inert to any fluids of the human body, for example, and can be constructed to be responsive to various desired phase transformation temperatures, Tg, above which the material is soft and reshapeable and then by cooling the material below the Tg, the material retains the reshaped configuration until it is again heated to above the Tg temperature at which time the SMP material returns to its original memory shape. Thus, by heating the SMP material, inserting therein an embolic platinum coil, or other device, applying pressure to the SMP material about the inserted coil while simultaneously or subsequently cooling, the coil is retained until released by again heating the SMP material to the temperature at which the material returns to its original shape. The heating of the SMP material can be carried out by resistive heating or by external field (RF magnetic induction) heating, or by light application thereto. Thus, a coil retained in an SMP microtube can be readily inserted via a catheter to a point of use, such as a brain aneurysm. The SMP microtubing can be inserted over or within an end of a delivery material, or provided with a light enhancing coating. The SMP microtubing can be manufactured, for example, to pass through passageways, such as blood vessels having inner diameters in the range of 250–1000 microns.

BRIEF DESCRIPTION OF THE DRAWINGS

The accompanying drawings, which are incorporated into and form a part of the disclosure, illustrate embodiments of the invention and an embodiment of a procedure for carrying out the invention and, together with the description, serve to explain the principles of the invention.

DETAILED DESCRIPTION OF THE INVENTION

Figure 1A:
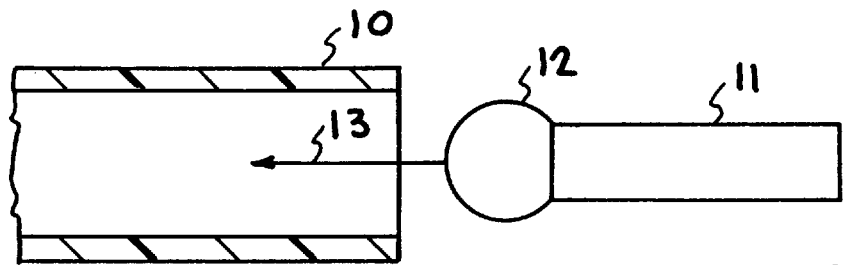
FIGS. 1A to 1E schematically illustrate the loading and release sequence for an object in a shape memory polymer (SMP) microtubular release mechanism.

The present invention is directed to microfabricated therapeutic actuators using shaped memory polymer (SMP) microtubing, and to heating mechanisms therefor. These miniature actuators are of particular interest for use within a small diameter passageways, such as blood vessels or arteries having diameters of about 500–1500 microns. The SMP microtubing may function, for example, as a release actuator mechanism for the delivery of embolic coils through catheters into aneurysms. These microfabricated actuators may also find use as a release mechanism for safety latches, connectors, assembly of read-write heads for disk drives, and various other medical and microassembly applications. Shape memory polymers distributed by Memry Corporation, can be formed into various configurations and sizes, and thus can be manufactured as small diameter microtubing capable of operating in a 500–1500 micron diameter arteries, blood vessel, or other passageway. SMP is a polyurethane-based material that undergoes a phase transformation at a manufactured temperature, Tg. After the material is polymerized (cross-linked), the material is molded into its memory shape. At a temperature above the Tg, the material is soft and can easily be arbitrarily reshaped by applying pressure into another configuration. The elastic constant of the material can change by about 200 times when undergoing this phase transformation. As the temperature is lowered, with the pressure applied, to a temperature below the Tg, this new shape is fixed and locked in as long as the material stays below the Tg. However, if the temperature reheats to above the Tg, the material will return to its original memory shape. The SMP material can be heated thermally by heated fluid, resistively, optically, and by external fold (radio frequency (RF) or magnetic induction) heating. The heating may be carried out by a laser light source via optical fibers, and with enhanced light absorption due to a coating on the SMP microtubing, an appropriate dye, or a doped polymer.

By inserting into an SMP microtubing, having a specified manufacture temperature, Tg, an end of an embolic platinum coil, for example, heating the microtubing to a temperature above the Tg, applying pressure to the microtubing causing it to conform to the configuration of the end of the coil, and then cooling to a temperature below the Tg, the end of the coil is retained or loaded in the SMP microtubing. By an inverted configuration the end of the SMP microtubing can be inserted into a hollow embolic coil and then heated. The SMP microtubing is then attached to the end of a guide wire or other guidance means and the platinum coil is loaded outside the body of a patient. The guide wire and the loaded coil are then pushed through a catheter in a blood vessel of the body, and at a desired point of use, a brain aneurysm or affected area, for example, the SMP microtubing is heated to a temperature above the Tg thereof, such as by injecting warm water through the catheter, resistive heating, external field heating, or optically heating, whereby the SMP microtubing returns to its original memory shape and the end of the coil is released at the desired point of use, whereafter the guide wire and attached SMP microtubing is removed via the catheter. The microtubing can be then cleaned for reuse or disposed of.

The microfabricated SMP release mechanism of this invention can improve the speed of release of the coil to seconds, compared to the previous 5–30 minutes with the currently used Guglielmi Detachable Coil described above, and is much more reliable with no known safety hazards to the patient. The release mechanism can also be used in other medical applications requiring the controlled deposition of therapeutic materials, as well as in various non-medical applications. The SMP tubing can be manufactured in various sizes and with different Tg temperatures, and thus its use as a release mechanism greatly expands the field of microdevices for numerous applications.

Figure 1B:
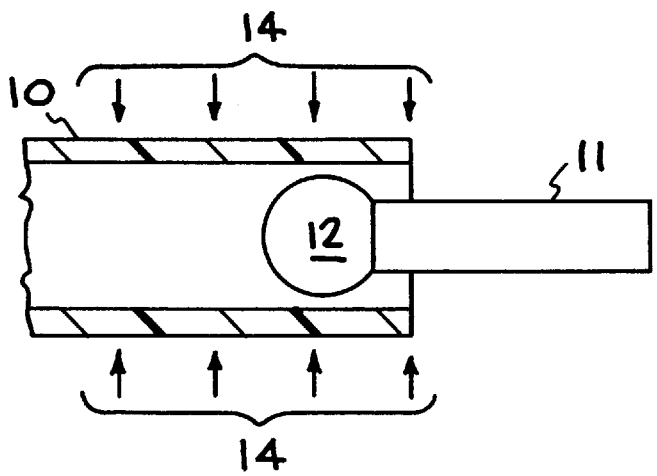
Figure 1C:
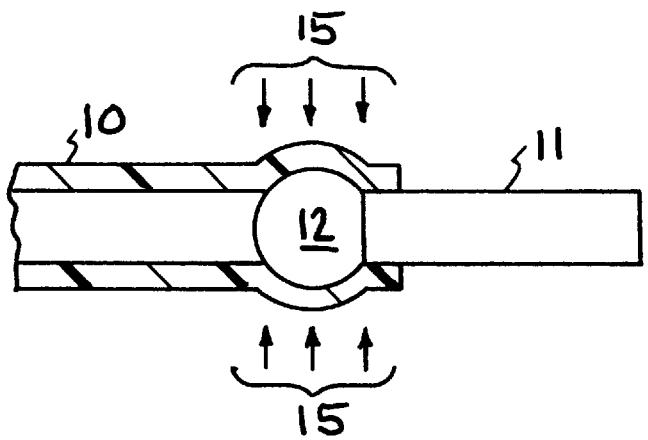
Figure 1D:
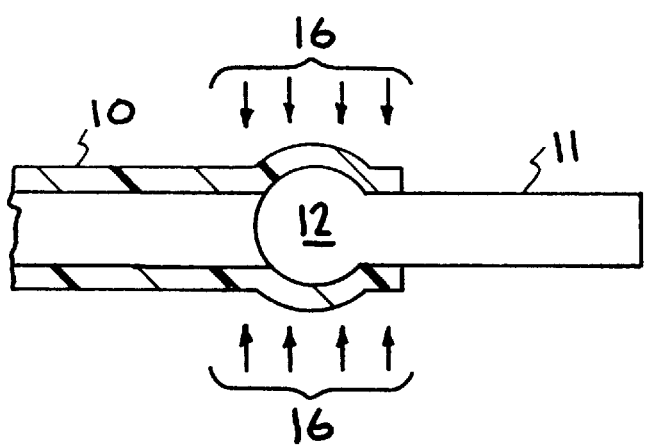
Figure 1E:
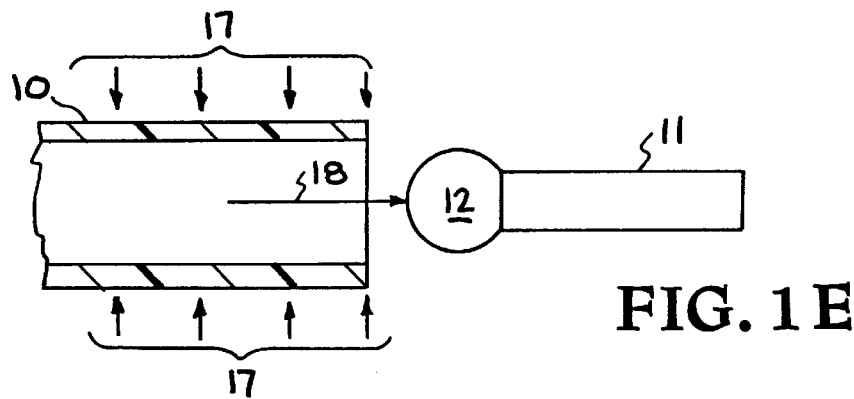

The following description, with reference to FIGS. 1A–1E, sets forth an example of the SMP microtubular release mechanism, and loading/release sequence, for use as a release mechanism for therapeutic material, such as an embolic platinum coil or other deposit material. A shape memory polymer (SMP) is manufactured to dimension and shape for an intended target or use, and with a specific phase transformation temperature, Tg. FIGS. 1A–1E illustrate the loading and release procedure of a straight SMP hollow member or tubing grabbing onto a coil with a ball end. In FIG. 1A the tubing or hollow member 10 is in its original size and shape and a coil 11 having a ball-end 12 can be loaded into the tubing 10 as indicated by arrow 13. The tubing 10 is heated above the Tg to soften the SMP material, as indicated at 14 in FIG. 1B, and then pressure is applied to the tubing 10 in the area of the ball-end 12, as indicated at 15 in FIG. 1C, whereby the tubing 10 is press-fitted over the ball-end 12 of coil 11. The joined ends of tubing 10 and coil 11 are then subjected to cooling to temperature below Tg, as indicated at 16 in FIG. 1D, which stiffens or hardens the SMP material and creates a solid hold of the ball-end 12 of coil 11 by the end of the SMP tubing 10. To release the coil 11 from SMP tubing, the joined area of the tubing 10 is simply reheated as indicated at 17 to above the Tg, the tubing 10 expands to its original opening and the coil 11 is released as indicated by arrow 18, as shown in FIG. 1E. The reheating of tubing 10 as indicated in FIG. 1E can be carried out by injecting warm water, for example, through the tubing. The tubing 10 can also be heated and/or reheated by resistive heating, optical heating, or thermal heating.

The amount of heating, pressure, cooling, and reheating is dependent of the diameter and Tg of the SMP tubing. For example, with an SMP tubing 10 having an internal diameter of 250 μm, an external diameter of 350 μm, and Tg of 45° C., with the coil 11 having a diameter of 200 μm with a ball-end 12 diameter of 250 μm, the SMP tubing is initially heated to a temperature of 48° C., and a pressure of 10 psi is applied to the tubing while maintaining the heat on the tubing to form the press-fit of the tubing around the ball-end of the coil. The SMP tubing is thereafter cooled to a temperature of 37° C., while maintaining the applied pressure, whereby the ball-end of the coil is fixedly retained in the SMP tubing. The coil is released from the SMP tubing by injecting water at a temperature of 48° C. through a surrounding tubing or catheter which causes the tubing temperature to raise above the Tg thereof. The SMP tubing can be fabricated with internal diameter of 100 μm to 1000 μm, an external diameter of 150 μm to 1 mm, and with a Tg in the range of –30° C. to 100° C.

FIGS. 2A–2D illustrate an embodiment of a shape memory polymer (SMP) gripper release mechanism wherein the gripping of the SMP tubing is inverted by inserting the SMP into a hollow end of a deposit material, such as a coil, to provide an inside out grip when the SMP is heated above the temperature Tg whereby the end of the SMP tubing is expanded to grip the inner surface of the coil, and thereafter inserting an optical fiber into an end of the SMP. The advantages are two-fold over the gripper release mechanism illustrated in FIGS. 1A–1E and disclosed in above-referenced application Ser. No. 08/807,412: 1) the SMP tubing occupies a minimal cross-sectional area (or diameter) which is critical to the intravascular applications to maneuver and manipulate in the smallest blood vessels; and 2) if released by optical fiber transmitted light, then the light is directly shown on the SMP and doesn't rely on indirect heat conduction, as through the deposit material.

Figure 2A:
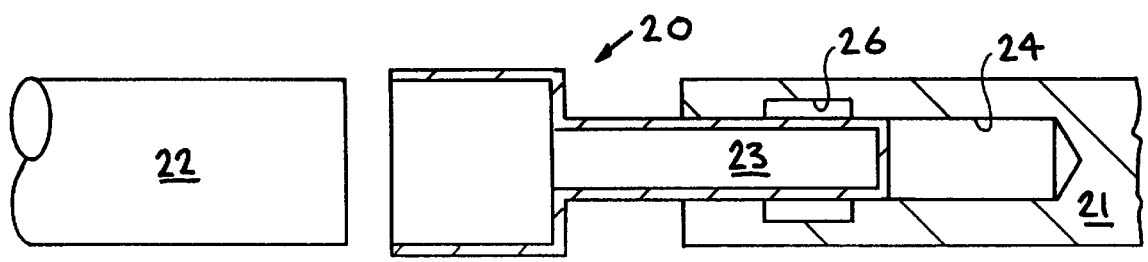
FIGS. 2A to 2D, illustrate another embodiment where the end of the SMP tubing is inserted into an end of a deposit material and then expanded to produce the desired grip on the deposit material.
Figure 2B:
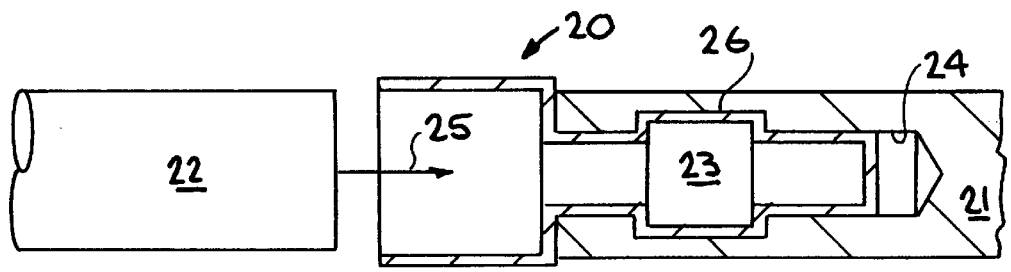
Figure 2C:
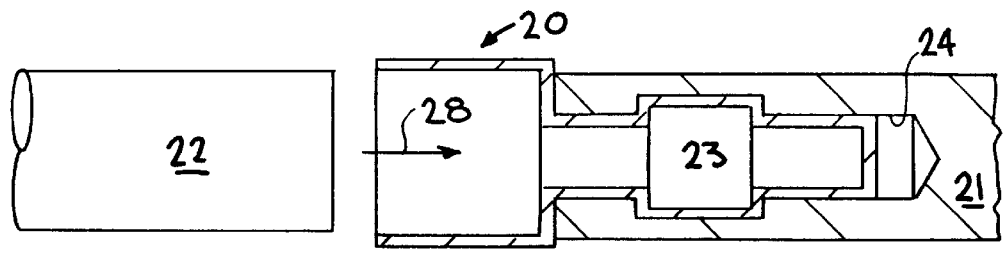
Figure 2D:
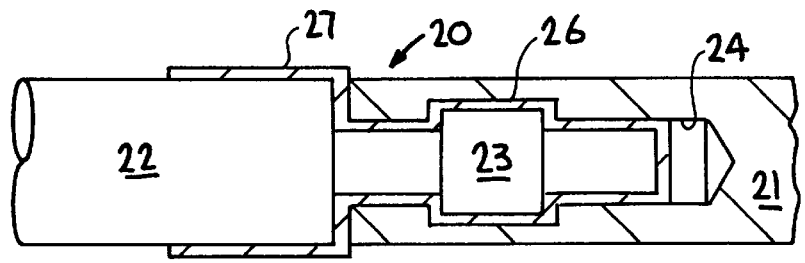

Referring now to FIGS. 2A–2D, which illustrate an embodiment of the inverted SMP grip and which is heated by laser light via an optical fiber release mechanism. The inverted SMP gripper release mechanism is composed of three components, an SMP balloon or tubing 20, a deposit material 21, and an optical fiber 22. The SMP tubing 20 includes a reduced diameter end section 23 which extends into an opening 24 in deposit material 21, as shown in FIG. 2A. Laser light, as indicated by arrow 25 is directed through optical fiber 22 into the interior of SMP tubing 20 thereby heating the tubing to a temperature above the Tg of the tubing, and pressure, such as a fluid, air or gas from a source not shown, is directed into the end section 23 of tubing 20 which forces end section 23 outwardly against the surface of the opening 24 in deposit material 21 and into a groove or enlarged diameter section 26 of opening 24, as shown in FIG. 2B, forming a gripping surface. The optical fiber 22 is then inserted into a larger diameter end section 27 of SMP tubing 20 as indicated by arrow 28 in FIG. 2C, after which a pressure is applied to the end section 27 to form a grip on the end of optical fiber 22, and the SMP tubing 20 is cooled below its temperature Tg thereby causing the tubing 20 to be retained in deposit material 21 and around an end of optical fiber 22, as shown in FIG. 2D. To release the deposit material, a light source, such as a laser, is again directed into the interior of end section 23 of SMP tubing 20 via optical fiber 22 to heat same above the temperature Tg of the SMP whereupon it reverts to its original shape (see FIG. 2A), thereby releasing the gripping action on the deposit material 21.

Figure 3A:
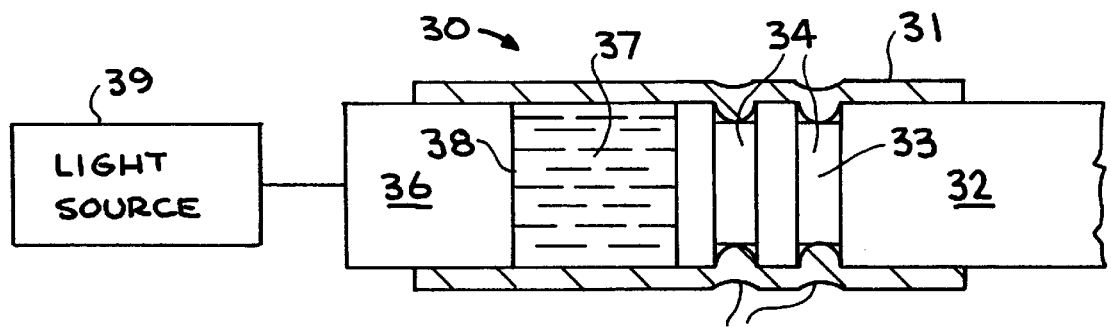
FIGS. 3A–3C and FIGS. 3D–3E illustrate heating arrangements for the SMP microtubular release mechanism.

FIGS. 3A to 3C and FIGS. 3D–3E illustrate embodiments of an SMP gripper mechanism utilizing a heat release mechanism which includes an absorbing dye chamber or resistive heater arrangements, such that once the dye or heater is heated, heat will be conducted to the SMP tubing and creeps into the gripping interface between the SMP tubing and the deposit material (e.g., a coil), causing the SMP tubing to be heated above its temperature Tg, whereafter pressure is applied and the SMP tubing is cooled, and upon reheating the SMP tubing returns to its original shape, releasing the gripping action of the deposit material. FIG. 3A utilizes heating of the dye chamber by a light source via an optical fiber, while FIGS. 3B, 3C, and 3D–3E illustrate different resistive heating mechanism. In addition, the heating of the dye chamber can be done by external field (radio frequency (RF) and magnetic induction) heating.

FIG. 3A illustrates an embodiment using an optical fiber to heat the dye chamber, and as shown the SMP gripper mechanism generally indicated at 30 which may be processed as described above in FIGS. 1A–1D, comprises an SMP tubing 31 retaining an object or deposit material 32, such as an embolic coil, having an end section 33 which is provided with a plurality of grooves 34. After insertion of the end section 33 of deposit material 32 and initial heating of SMP tubing 31, as shown in FIGS. 1A–1B, and applying pressure about the grooves 34 of end section 33 and cooling of the SMP tubing 31, as shown in FIGS. 1C–1D, the material of SMP tubing 31 is indented or deformed and extends into the grooves 34, as indicated at 35, which provides a more secure grip or retention of the end section 33 of deposit material 32 than the ball-end 12 of coil 11 in FIGS. 1A–1D, due to the grooved arrangement of end section 33. In FIG. 3A, after the deposit material 32 has been loaded into SMP tubing 31, the SMP tubing 31 is attached, as by the heating, pressure, cooling process described above, to an optical fiber 36, or to a catheter tube having one or more optical tubes therein, so as to define a space in which a chamber 37 located between an end 38 of optical fiber 36 and end section 33 of deposit material 32. The chamber 37 contains a heat absorbing dye and thus defines a dye chamber. The dye chamber 37 and optical 36 define a heating mechanism which functions to release the deposit material (coil) 32 from SMP tubing 31, as described above relative to FIG. 1E. The heating mechanism (36–37) operates by light, such as from a laser light source 39, directed through optical fiber 36 into the dye in dye chamber 37 which heats the dye. Once the dye in chamber 37 is heated, heat will be conducted to the SMP tubing 31 and into the invented areas 35 in grooves 34 of deposit material 32. Upon heating of the SMP tubing indented sections 35 above the temperature Tg thereof, the SMP material will revert or return to its original shape, whereby the indented sections 35 of SMP tubing 31 is withdrawn from grooves 34 in the deposit material 32 and the gripping action of the SMP material is removed, whereby the SMP tubing 31 and be withdrawn from the deposit material 32 leaving the deposit material at a desired location, such as in a blood vessel of a human body. By way of example, with the SMP tubing 31 having a temperature Tg of 55° C., and using a dye having pigment dispersions in chamber 37, a light having an energy of 100 mW directed through optical fiber 36 heats the dye to a temperature of 60° C., above the temperature Tg in a time period of 1 to 5 seconds, whereby the SMP tubing indented sections 35 revert to original shape in a time period of 0.5 to 5 seconds. For example, the light source 39 may be a diode pumped laser operating at a wavelength of 400 to 1500 nm.

Figure 3B:
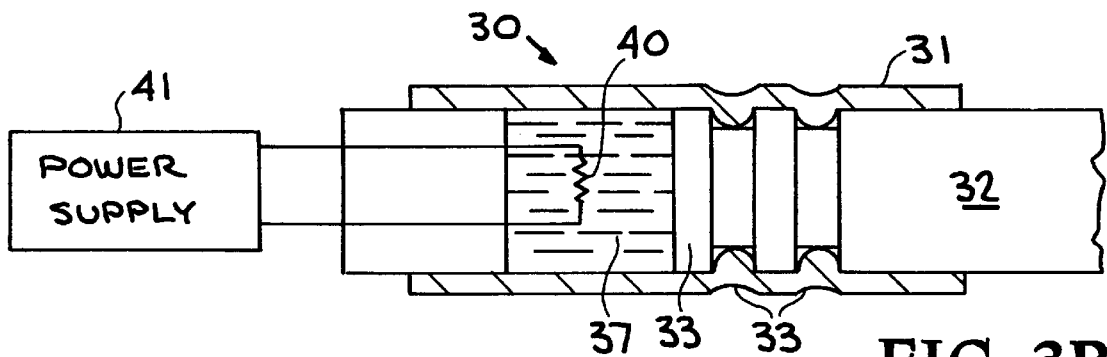

FIG. 3B illustrates an embodiment similar to FIG. 3A except for the use of a fluid instead of a dye and the heating mechanism which is of a resistive type, and thus corresponding components will be given similar reference numbers. Here, the chamber 37 may contain a fluid, such as water, or a gas and is located within SMP tubing 31 adjacent the end section 33 of deposit material 32. It is to be understood that the SMP tubing 31 is secured to a tube, catheter, guide wire, etc., not shown, for insertion of the deposit material 32 to a point of use. In FIG. 3B, a resistor 40, in the form of a coil in this embodiment, is positioned in dye chamber 37 and adapted to be connected to an electrical power supply 41, which functions to heat the fluid in chamber 37 to a temperature sufficient to heat the SMP tubing to a temperature above its Tg, thus releasing the deposit material 32 as described above. By way of example, the resistor coil 40 may be composed of titanium or gold having a diameter of 15 to 25 μm, with the power supply 41 being of a direct current or alternating current type producing a current of 1 to 50 mA through the resistor coil 40. With water in the chamber 37, and with a current flow of 1 mA through resistor coil 40, a time period of 1 to 2 seconds would be required to cause release of the deposit material.

Figure 3C:
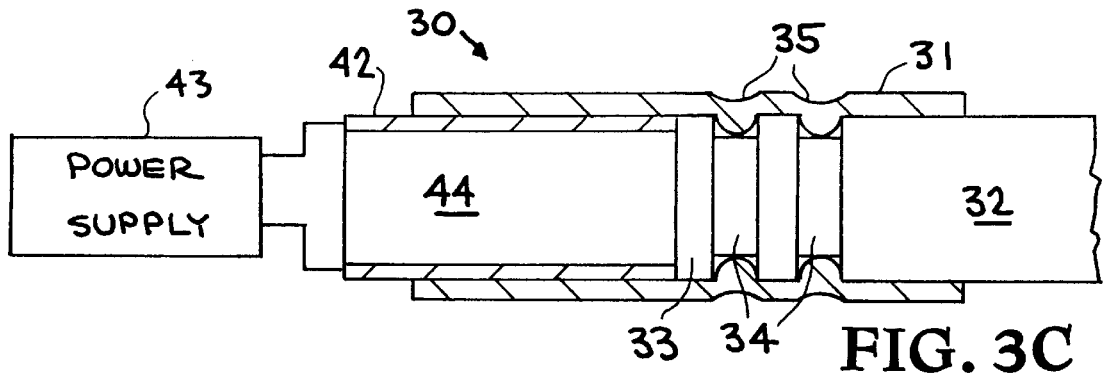

FIG. 3C illustrates an embodiment similar to FIG. 3B except the heating chamber is omitted and in the type of resistor utilized in the heating mechanism, and similar components are given similar reference numerals. The SMP tubing is to be connected to a guide wire 44. Here, an embedded resistor 42 is utilized which is embedded in the inner surface of SMP tubing 31 or can be secured to the inner surface thereof. The embedded resistor 42 is attached to an electrical power supply 43 for heating the SMP tubing 31. The embedded resistor 42 may, for example, be composed of a thin layer (0.5 to 5.0 μm) of Ti, Au, or Pt, and carry an electrical current of 1 to 10 mA. The heating time for release of the deposit material is about the same as that of FIG. 3B.

Figure 3D:
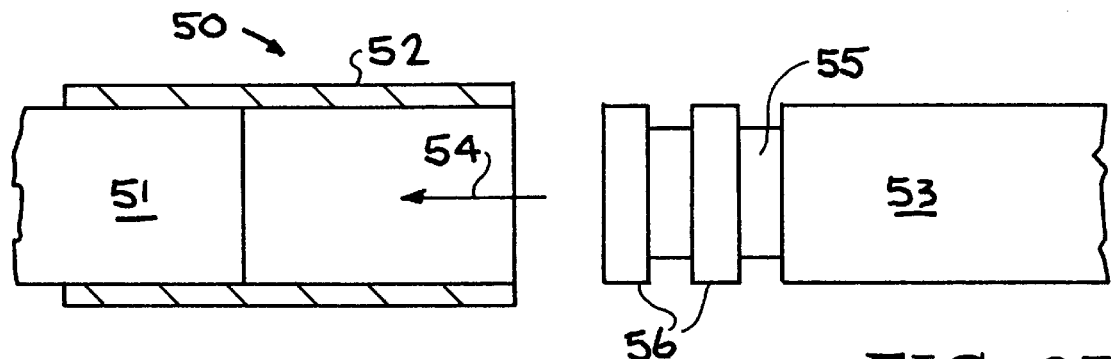
Figure 3E:
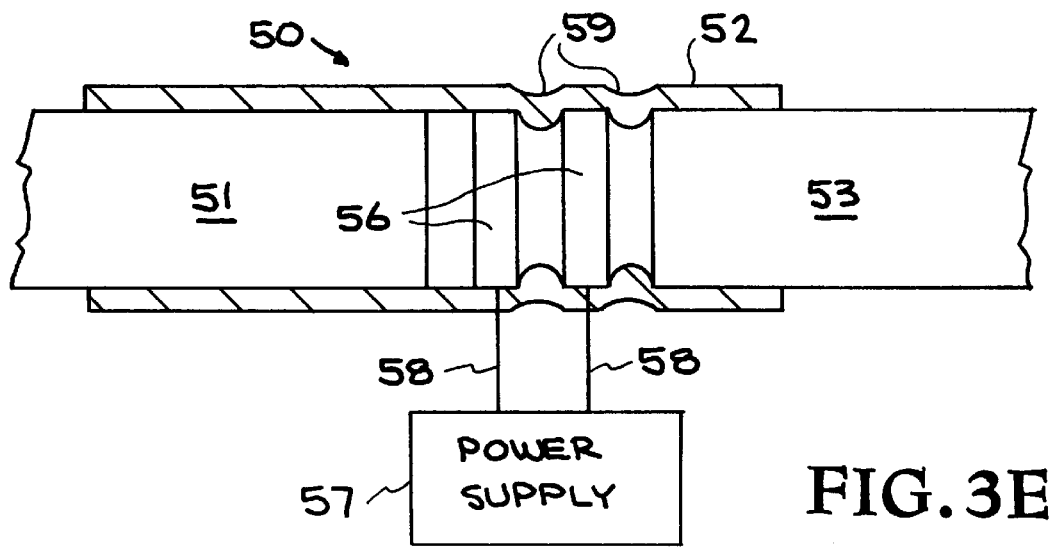

FIGS. 3D and 3E illustrate an embodiment wherein a deposit material is inserted into an end of an SMP tubing, then a guide wire containing resistive heating coils is inserted into an opposite end of the SMP tubing, and thereof the SMP tubing is heated, pressurized and cooled to form a grip on the guide wire. As shown, the grip/release mechanism generally indicated at 50, has a deposit material 51, such as an embolic coil, which is inserted into an end of an SMP tubing 52, and thereafter a guide wire 53 is inserted into the opposite end of tubing 52 as indicated by arrow 54 in FIG. 3D. The guide wire 53 has a reduced diameter end section 55 on which is mounted a pair of resistive heating coils 56. With the guide wire 53 and heating coils 56 inserted into the SMP tubing 52, the tubing is heated by coils 56, connected to a power supply 57 by electrical leads 58, as schematically illustrated in FIG. 3E. After heating of the tubing 52 to a temperature above the Tg of the tubing, pressure is applied to the tubing to form indentations 59 whereby the tubing material is reshaped to conform to the surfaces or grooves defined by coils and end section 55 of guide wire 53, as shown in FIG. 3E, and then the SMP tubing is cooled below its Tg, as described above. In actual practice, the electrical leads connecting power supply 57 to coils 56 may extend along the surface of the guide wire and contact the coils, or among an inner surface of the SMP tubing so as to contact the coils when the coils and guide wire are inserted into the SMP tubing. The heating coils 56 may be constructed of any suitable resistive material, such as Au wires having a diameter of 5 μm and wrapping of 5–20 turns, which produces heat when an electric current is passed therethrough. By way of example, the leads 58 may be formed of 5 to 20 μm diameter wire composed of Ti, Au, or Pt.

Figure 4:
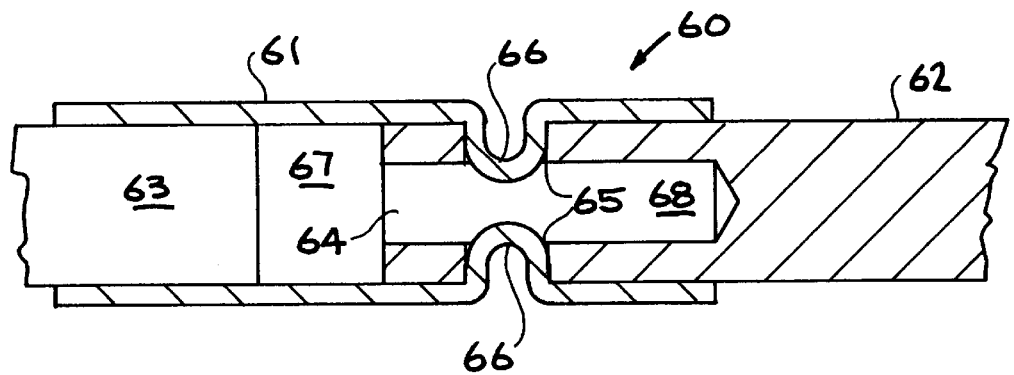
FIG. 4 illustrates an embodiment with a light trap release arrangement.

FIG. 4 illustrates an embodiment of a SMP gripper mechanism having a heating mechanism utilizing an optical fiber and a light trap formed in the SMP tubing and deposit material. As shown, the gripper mechanism generally indicated at 60 includes an SMP tubing 61, a deposit material 62, and an optical fiber 63. The deposit material 62 is provided with a central opening 64 and a plurality of radial openings 65, only two shown. The deposit material 62 is gripped by indentations 66 of SMP tubing 61 which extend into radial openings 65 of the deposit material, the gripping indentations 66 being formed as discussed above by the heating, pressure, cooling process illustrated in FIGS. 1A–1D. The optical fiber 63 may be slip-fit into the SMP tubing 61 or the tubing can be processed to grip the optical fiber. The optical fiber 63, in this embodiment, is located in a spaced relation to deposit material 62 to define a space or chamber 67, which in combination with central opening 64 of deposit material 62 forms a light trap indicated at 68. Here the light trap 68 forms the heating mechanism for heating the indentations 66 of SMP tubing 61 to release the deposit material 62 from the gripping action of the SMP tubing 61. Here, light is directed into light trap 68 via optical fiber 63 from a light source such as described above with respect to FIG. 3A.

Figure 5:
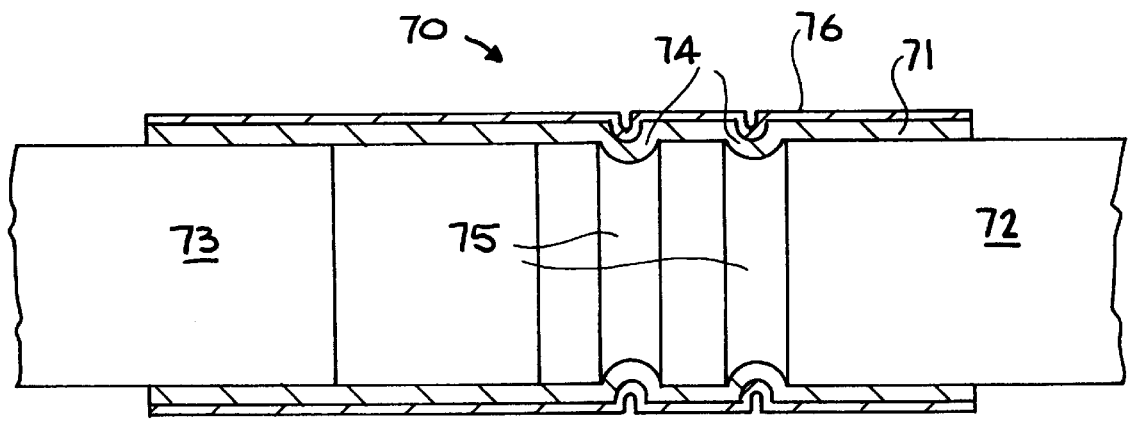
FIG. 5 illustrates an embodiment utilizing a reflective coating for optical fiber heating by a laser light source.

FIG. 5 illustrates an embodiment of an SMP gripper mechanism which utilizes a thin metallic coating or film on the exterior surface of the SMP tubing for enhanced reflectivity and for increasing hoop strength, whereby the heat release mechanism may be by external field (RF, magnetic induction) heating, or by optical fiber heating by a laser power source, for example. As shown in FIG. 5, the gripper mechanism 70, which is generally similar to FIG. 3A except for the omission of the dye chamber, includes an SMP tubing 71 gripping a deposit material 72 in one end and having an optical fiber 73 secured in an opposite end, with the SMP tubing 71 having indentations 74 which extend into grooves 75 of deposit material 72 to produce a gripping action, as described above. The SMP tubing 71 is provided with a thin metallic coating or film 76, which may be composed of Ti, Au, or Pt and have a thickness of 1 to 5 µm on the external surface thereof. In this embodiment which utilizes light via optical fiber 73 as the heating release mechanism, as previously described, the thin film or metal coating 76 provides enhanced reflectivity within the SMP tubing 71 by preventing light loss outside the SMP material, which increases the efficiency of the heating release mechanism.

It is also possible to externally heat the SMP tubing of the embodiment of FIG. 5 by RF or magnetic induction (external field heating) by forming the thin metallic coating 76 of selected materials, such as Pd—Ni, Fe—Ni, or Pt.

It has thus been shown that the present invention provides additional approaches to SMP gripper mechanisms and to heating release mechanisms for SMP gripper mechanisms, thus advancing the state-of-the-art beyond the SMP gripper mechanisms described and claimed in above-referenced U.S. application Ser. No. 08/807,412. The SMP tubing may be utilized for internal (inverted) gripping and may be coated with a material for enhancing heating by light absorption in the SMP material by preventing light loss outside the SMP material, or the SMP tubing may be coated with a metallic material which enables heating of the SMP material by external field heating (RF and magnetic induction). The heating release mechanism may include a dye chamber, with the dye being heated by light absorption or resistive/heating, or by the use of a light trap.

While particular embodiments, materials, etc., have been described and/or illustrated to exemplify the invention and describe the principles of the invention, and such are not intended to be limiting. Modifications and changes may become apparent to those skilled in the art, and it is intended that the invention be limited only by the scope of the appended claims.

The invention claimed is:

1. In a release mechanism having means adapted for retaining therein and releasing therefrom an object, the improvement comprising:

said means being composed of a shape memory polymer material; and a heating release mechanism for said material, said shape memory polymer material undergoes a phase transformation at a temperature Tg, whereby heating said material above the temperature Tg enables the material to soften and be reshaped to another configuration, and cooling of the material below the temperature Tg causes the material to stiffen and retain the reshaped configuration until the material is reheated to above the temperature Tg causing the material to return to its original shape.

2. The improvement of claim 1, wherein said heating release mechanism includes means for reheating of the material from a group of heating sources consisting of thermal heating, heated fluid, resistive heating, external field heating, and optical heating.

3. The improvement of claim 1, wherein said temperature Tg is in the range of −30° C. to 100° C.

4. The improvement of claim 1, wherein said shape memory polymer material is provided with a metallic coating on an outer surface thereof.

5. The improvement of claim 1, wherein said heating release mechanism includes a dye chamber.

6. The improvement of claim 1, wherein said heating release mechanism is selected from the group consisting of a dye chamber, a light trap, a metallic coating on the shape memory polymer, a dye chamber and a light means for heating dye in said dye chamber, a fluid chamber and an electrical resistor for heating fluid in said chamber, and a plurality of resistive coils.

7. The improvement of claim 1, wherein said heating release mechanism includes a metallic coating on the shape memory polymer material.

8. The improvement of claim 1, wherein said heating release mechanism includes a dye chamber and a light means for heating dye in said dye chamber.

9. The improvement of claim 1, wherein said heating release mechanism includes a fluid chamber and an electrical resistor for heating fluid in said chamber and thereby heating the shape memory polymer material.

10. The improvement of claim 1, wherein said heating release mechanism includes a plurality of resistive coils.

11. The improvement of claim 1, wherein said heating release mechanism is selected from the group consisting of optical heating, resistive heating, and external field heating.

12. In a shape memory polymer gripper mechanism for retaining and releasing an associated object, the improvement comprising:

a heating release mechanism, said shape memory polymer undergoes a phase transformation at a temperature Tg, whereby heating said material above the temperature Tg enables the material to soften and be reshaped to another configuration, and cooling of the material below the temperature Tg causes the material to stiffen and retain the reshaped configuration until the material is reheated to above the temperature Tg causing the material to return to its original shape.

13. The improvement of claim 12, wherein said heating release mechanism includes heating means selected from the group consisting of optical heating resistive heating, and external field heating.

14. The improvement of claim 13, wherein said heating release mechanism additionally includes a dye chamber for heating the shape memory polymer material.

15. The improvement of claim 13, wherein said heating release mechanism includes a light trap.

16. The improvement of claim 13, wherein said heating release mechanism includes a coating of material on a surface of the shape memory polymer material.

17. The gripper mechanism of claim 12, wherein said shape memory polymer is configured to extend into an object for retaining and releasing such an object.

18. The gripper mechanism of claim 12, wherein the associated object comprises a deposit material, and wherein said deposit material has an opening therein having different diameter sections, and wherein said shape memory polymer comprises a tubing having a reduced diameter end section extending into said different diameter sections of said opening in said deposit material.

* * * * *